United States Patent [19]

Rechenberg

[11] 4,247,351
[45] Jan. 27, 1981

[54] PROCESS FOR MANUFACTURING ARTIFICIAL BREASTS

[76] Inventor: Cornelius Rechenberg, Weidach 22, 8204 Brannenburg, Fed. Rep. of Germany

[21] Appl. No.: 933,167

[22] Filed: Aug. 14, 1978

[30] Foreign Application Priority Data

Aug. 18, 1977 [DE] Fed. Rep. of Germany ....... 2737321

[51] Int. Cl.³ .......................... B29F 1/00; A61F 1/00; A41C 3/14
[52] U.S. Cl. .......................................... 156/221; 3/36; 128/481; 156/244.19; 156/244.22; 156/245; 264/46.6; 264/46.8; 264/261; 428/447
[58] Field of Search ........... 156/245, 145, 221, 244.19, 156/244.22; 264/46.6, 46.8, 261; 128/463, 479, 481; 3/36; 428/447

[56] References Cited

U.S. PATENT DOCUMENTS 4,116,736  9/1978  Sanson et al. ........................... 156/79
4,172,298  10/1979  Rechenberg ............................... 3/36

FOREIGN PATENT DOCUMENTS 2605148  8/1977  Fed. Rep. of Germany .

Primary Examiner—William A. Powell
Assistant Examiner—Robert A. Dawson
Attorney, Agent, or Firm—Howard C. Miskin

[57] ABSTRACT

A process for manufacturing artificial breasts using a two component silicone rubber composition capable of a cross linking additional reaction, has cups sheathed by a plastic layer joined by welding and into which the composition is charged under pressure, and during the vulcanization the edges of the sheets are forced together and joined by welding and the protruding edge portion cut off.

3 Claims, 1 Drawing Figure

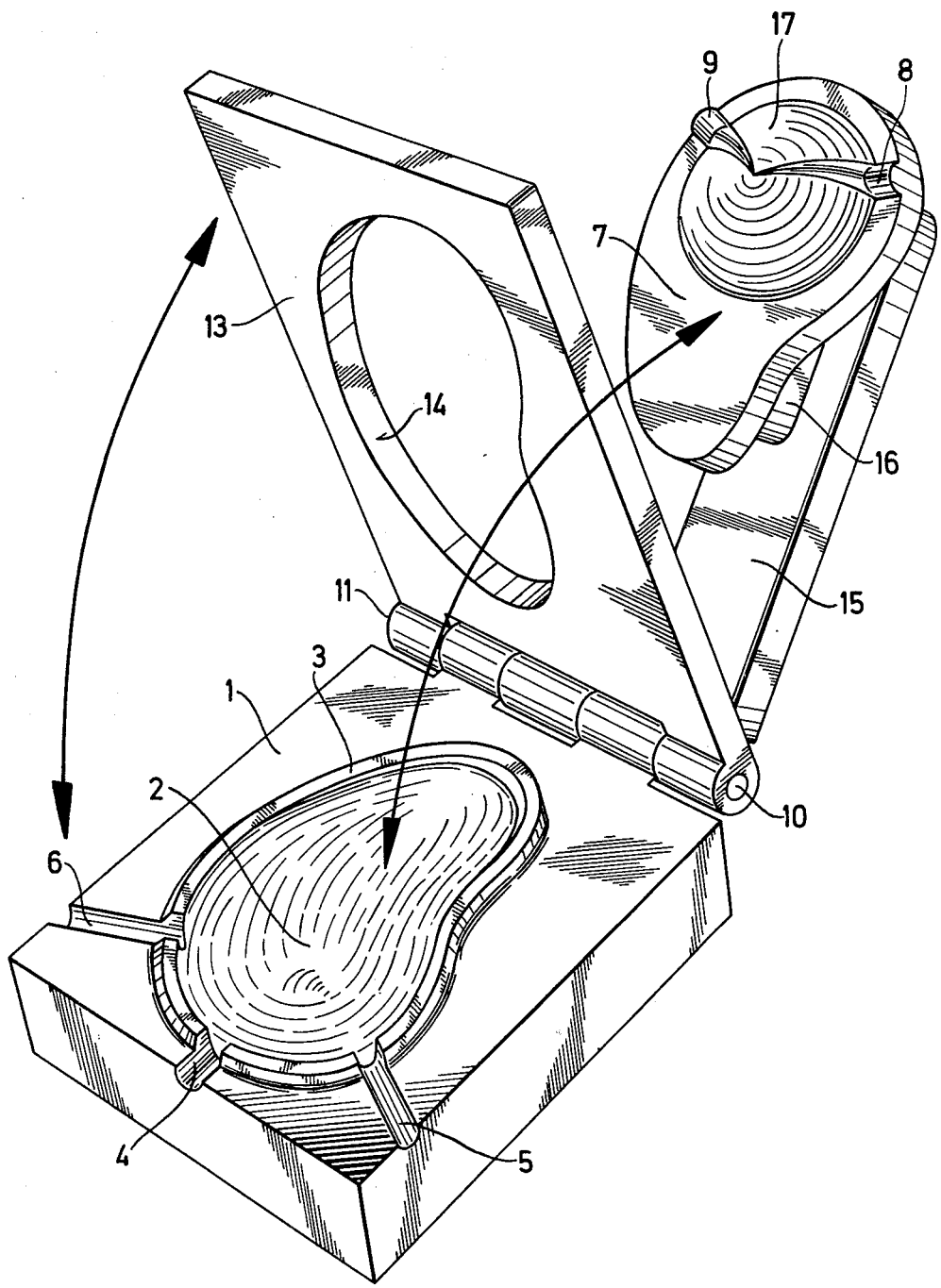

PROCESS FOR MANUFACTURING ARTIFICIAL BREASTS

This invention relates to a process of manufacturing artificial breasts comprising breast-shaped cups made from a two-component silicone rubber composition capable of a cross-linking addition reaction, which cups are sheathed by plastic sheeting layers joined by welding, in which process the flat-lying sheathing layers are superimposed and secured to a mold base part having a cavity which conforms to the breast, the mold base part is closed by a cover which has a rear surface which adjacent to said cavity conforms to the contour of the rear side of the artificial breast, the two-component silicone rubber composition is charged under pressure into a narrow region between the sheeting layers until the composition has forced the sheeting layers against the surfaces which define the mold cavity, and the composition is then vulcanized in the mold under the action of heat. The invention relates also to apparatus for carrying out that process.

Patent application P 27 01 627.9 discloses a process which is of the kind described first hereinbefore and in which the sheeting layers which form the sheath of the artificial breast are first joined by welding, except for a filling opening, along a line intended to form the edge of the artificial breast. It is difficult, however, to secure the welded sheeting layers to the base part of the mold in such a manner that the seam weld lies on the edge of the cavity formed in the base part of the mold. Even when the edge of the cavity is coated with a non-curing adhesive, a certain dexterity is required to apply the welded sheeting layers to the base part of the mold in the proper position. Besides, even though the sheeting layers may have been properly applied initially, they may shift or become distorted during the subsequent process steps so that defective artificial breasts result and rejects are produced.

It is an object of the present invention to simplify the placing of the sheeting layers in the mold used to manufacture the artificial breasts, to enable the manufacture of the artificial breasts at lower costs and to avoid rejects.

In a process of the kind described first hereinbefore, this object is accomplished in that the layers which have not yet been joined by welding are forced together between the edge of the cavity in the mold base part and the cover overlying said edge and are joined by welding adjacent to their edges during the vulcanization at temperatures at which the sheeting is molten, and the protruding edge portion is cut off. Because in the process according to the invention the sheeting layers which form the sheath of the artificial breast are joined by a seam weld during the vulcanization of the two-component silicone rubber composition, it is not necessary exactly to align the sheeting layers as they are placed in the mold.

It is apparent that the process according to the invention simplifies the manufacture and avoids rejects.

Where the preferred polyurethane sheeting is used, the melting and welding are effected in a temperature range of 180° to 230° C.

In accordance with the invention, apparatus for carrying out the process according to the invention is characterized in that a stretching frame is adapted to be placed onto the base part of the mold so that said frame surrounds the cavity and is spaced from the latter by a distance corresponding to the width of the subsequent seam weld and the cover is adapted to be inserted into the opening of the stretching frame so as to be supported on the edge of the cavity. The superimposed sheeting layers are held in position by the stretching frame, which lies flat on the base part of the mold so that the sheeting layers cannot be shifted or distorted as the cover is applied.

According to a preferred feature of the invention, the base part of the mold has a raised rim, which surrounds the cavity and has the same width as the seam weld, a stretching frame for securing the sheeting layers is adapted to be placed on the base part of the mold and has an opening having a contour which fits the outside contour of the raised rim so that the frame fits around the raised rim, and the cover is a clearance fit in the opening and is supported on the rim and adapted to be locked in the opening. A simple operation will be enabled if the stretching frame and the cover are hinged to the base part of the mold. The cover may be alternatively hinged to the stretching frame.

The raised edge portion may be provided on the outside with a sharp edge for severing the sheeting layers as they are welded.

The inner edge of the stretching frame or the outer edge of the cover, depending on which part is lifted first after the vulcanization, may form a template for guiding a knife used to cut off the edge portions with which the sheeting layers protrude from the seam weld.

According to a further feature of the process according to the invention, the sheeting layers gripped in the mold are first inflated by means of air or gas until they engage the surfaces defining the mold cavity. The mold is then heated to the melting temperature of the sheeting in order to form the seam welds and is then cooled and vented, the two-component silicone rubber composition is then charged into the sheath formed by the thus pretensioned sheeting layers and the interior of the sheath is vented at the same time, whereby the sheath is caused to again contact the surfaces defining the mold cavity, and the mold is subsequently reheated to accelerate the curing.

In experiments it has been found that artificial breasts having a sheath that is smooth and free from wrinkles can be made if the sheath is pre-tensioned and is welded in a tensional state. When the sheath for the artificial breast has been pre-tensioned by inflating air or an inflating gas, a residual tensile stress will remain in the sheeting layers and will cause them to disengage from the surfaces defining the mold cavity when the sheath is vented. When the silicone rubber composition is then introduced into the pretreated sheath, the charging pressure will cause the sheath to be slightly stretched until it engages the surfaces defining the mold cavity so that the surface of the artificial breast will be smooth and free from wrinkles. The silicone rubber composition may be charged one in the other. The inner flexible tubing may be used for venting and the annular passage may be used to supply the plastic composition, or vice versa. The two-component silicone rubber composition is preferably cured at temperatures below the melting point of the sheeting so that a certain stress is preserved in the sheath of the artificial breast.

An embodiment of the invention will be explained more fully and by way of example with reference to the single FIGURE of the drawing, which is a diagrammatic perspective view showing a mold for making an artificial breast.

The base part 1 of the mold used to manufacture artificial breasts is formed with a cavity 2, which conforms to the outside surface of the artificial breast. The flat top surface of the mold base part 1 is provided with a raised annular rim 3, which surrounds the cavity 2 and has the same width as the seam weld which joins the sheath of the artificial breast. A groove 4 is formed in the top surface of the mold base part 1 and serves to receive the flexible tubing, which opens between the sheeting layers and serves to charge the two-component silicone rubber composition. Two further grooves 5, 6 are formed in the mold base part 1 and serve to receive ribs 8, 9, which are provided on the cover 7 and cause recesses to be formed at the edge of the artificial breast.

By means of hinges 10, 11, the mold base part 1 is connected to a stretching frame 13, which can be swung down onto the mold base part 1 so that the raised rim 3 is received in the opening 14 of the frame. By means of a connecting member 16, the cover 7 is secured to a carrier, which is hinged to the mold base part 1. The cover 7 has an elevation 17, which causes a cavity to be formed in the artificial breast at the rear thereof. The cover 7 can be swung into the opening 14 of the stretching frame 13 so that the cover is supported by the raised rim 3 of the mold base part 1.

The mold base part is provided with venting bores which open into its cavity. The stretching frame 13 and the cover 7 may consist of transparent silicone rubber.

The stretching frame 13 and the cover 7 which have been swung down onto the mold base part 1 may be retained in position by suitable locking means, not shown. The pivotal movements of the stretching frame 13 and of the cover 7 are indicated by curved double-headed arrows.

The mold is charged as has been described in the prior application mentioned above. Vulcanization is effected at higher temperatures, at which the sheeting layers are joined by welding to form a sheath of the artificial breast. The use of higher temperature affords the advantage that the vulcanization time can be greatly shortened.

The filling opening left in the welded edge is closed is closed by welding when the artificial breast has been removed from the mold.

While there has been described and illustrated a preferred embodiment of the present invention, it is apparent that numerous alterations, omissions and additions may be made without departing from the spirit thereof.

I claim:

1. A process of manufacturing artificial breasts comprising breast-shaped cups made from a two-component silicone rubber composition capable of a cross-linking addition reaction, which cups are sheathed by plastic sheeting layers joined by welding, in which process the flat-lying sheathing layers are superimposed and secured to a mold base part having a cavity which conforms to the breast, the mold base part is closed by a cover which has a rear surface which adjacent to said cavity conforms to the contour of the rear side of the artificial breast, the two-component silicone rubber composition is charged under pressure into the region between the sheeting layers until the composition solely under the influence of said charging pressure has forced the sheeting layers against the surfaces which define the mold cavity, the composition is then vulcanized in the mold base part and the cover overlying said edge and are joined by welding adjacent to their edges before the completion of the vulcanization at temperatures at which the sheeting is molten, and the protruding edge portion is cut off.

2. A process according to claim 1, characterized in that the sheeting layers gripped in the mold are first inflated by means of air or gas until they engage the surfaces defining the mold cavity, mold is then heated to the melting temperature of the sheeting in order to form the seam welds and is then cooled and vented to pretension the sheeting layers and retract them from the cavity surfaces the two-component silicone rubber composition is then charged into the sheath formed by the thus pretensioned sheeting layers and the interior of the sheath is vented at the same time, whereby the sheath is caused to again contact the surfaces defining the mold cavity, and the mold is subsequently reheated to accelerate the curing.

3. A process according to claim 1 wherein said sheathing layers are welded together during the vulcanization of said two-component silicone rubber composition.

* * * * *

UNITED STATES PATENT OFFICE
CERTIFICATE OF CORRECTION

PATENT NO. : 4,247,351

DATED : January 27, 1981

INVENTOR(S) : CORNELIUS RECHENBERG

It is certified that error appears in the above-identified patent and that said Letters Patent are hereby corrected as shown below:

Amend Claim 1 as follows:

--1 A process of manufacturing artificial breasts comprising breast-shaped cups made from a two-component silicone rubber compositon capable of a cross-linking addition reaction, which cups are sheathed by plastic sheeting layers joined by welding, in which process the flat-lying sheathing layers are superimposed and secured to a mold base part having a cavity which conforms to the breasts, the mold base part is closed by a cover which has a rear surface which adjacent to said cavity conforms to the contour of the rear side of the artificial breast, the two-component silicone rubber compositon is charged under pressure into the region between the sheeting layers until the composition solely under the influence of said charging pressure has forced the sheeting layers against the surface which define the mold cavity, the composition is then vulcanized in the mold <u>under the action of heat, characterized in that the layers which have not yet been joined by welding are forced together between the edge of the cavity in the mold</u> base part and the cover overlying said edge and are joined by welding adjacent to their edges before the completion of the vulcanization at temperatures at which the sheeting is molten, and the protruding edge portion is cut off.--

Signed and Sealed this

Twenty-third Day of June 1981

[SEAL]

Attest:

RENE D. TEGTMEYER

*Attesting Officer*     *Acting Commissioner of Patents and Trademarks*